United States Patent [19]

Tan et al.

[11] Patent Number: 4,682,290

[45] Date of Patent: Jul. 21, 1987

[54] METHOD OF RECONSTRUCTING A HIGH RESOLUTION IMAGE BY TOMODENSITOMETRY

[75] Inventors: Siv C. Tan, Paris; Didier Le Galle, Jouy en Josas; Claude Benchimol, Paris, all of France

[73] Assignee: Thomson - CGR, Paris, France

[21] Appl. No.: 716,354

[22] Filed: Mar. 26, 1985

[30] Foreign Application Priority Data

Mar. 30, 1984 [FR] France .................. 84 05042

[51] Int. Cl.$^4$ .................. G06F 15/42; G06F 15/52
[52] U.S. Cl. .................. 364/414; 378/901; 382/6
[58] Field of Search .................. 364/414, 577, 578; 378/901, 19; 358/138; 382/6

[56] References Cited

U.S. PATENT DOCUMENTS

| 4,042,811 | 8/1977 | Brunnett et al. | 378/901 |
| 4,144,570 | 3/1979 | Wagner | 378/901 |
| 4,280,178 | 7/1981 | Nàssi et al. | 378/901 |
| 4,555,760 | 11/1985 | Op de Beck et al. | 364/414 |

FOREIGN PATENT DOCUMENTS 1474685 5/1977 United Kingdom .
1577046 10/1980 United Kingdom .

Primary Examiner—Charles E. Atkinson
Assistant Examiner—Kimthanh T. Bui
Attorney, Agent, or Firm—Roland Plottel

[57] ABSTRACT

A method for reconstructing a high resolution image by interpolating intermediate values obtained from data collected over a complete revolution of the tomodensitometer. A shift of $$\left| \frac{\Delta \gamma}{4} \right|$$

is provided between the middle of the multi detector and the straight line joining the focal point of the X rays and the center of rotation and the views $V_i$ collected over a complete revolution are completed from "views" $V'_i$ resulting from a transformation:

$$T(\theta,\gamma))(\theta+(2k-1)\pi,-\gamma),$$

the intermediate values $s_i$ being obtained by linear interpolation from samples of the views $V'_i$ of the same ordinate $\gamma$, in the space $[\theta,\gamma]$ and situated on each side thereof respectively.

2 Claims, 8 Drawing Figures

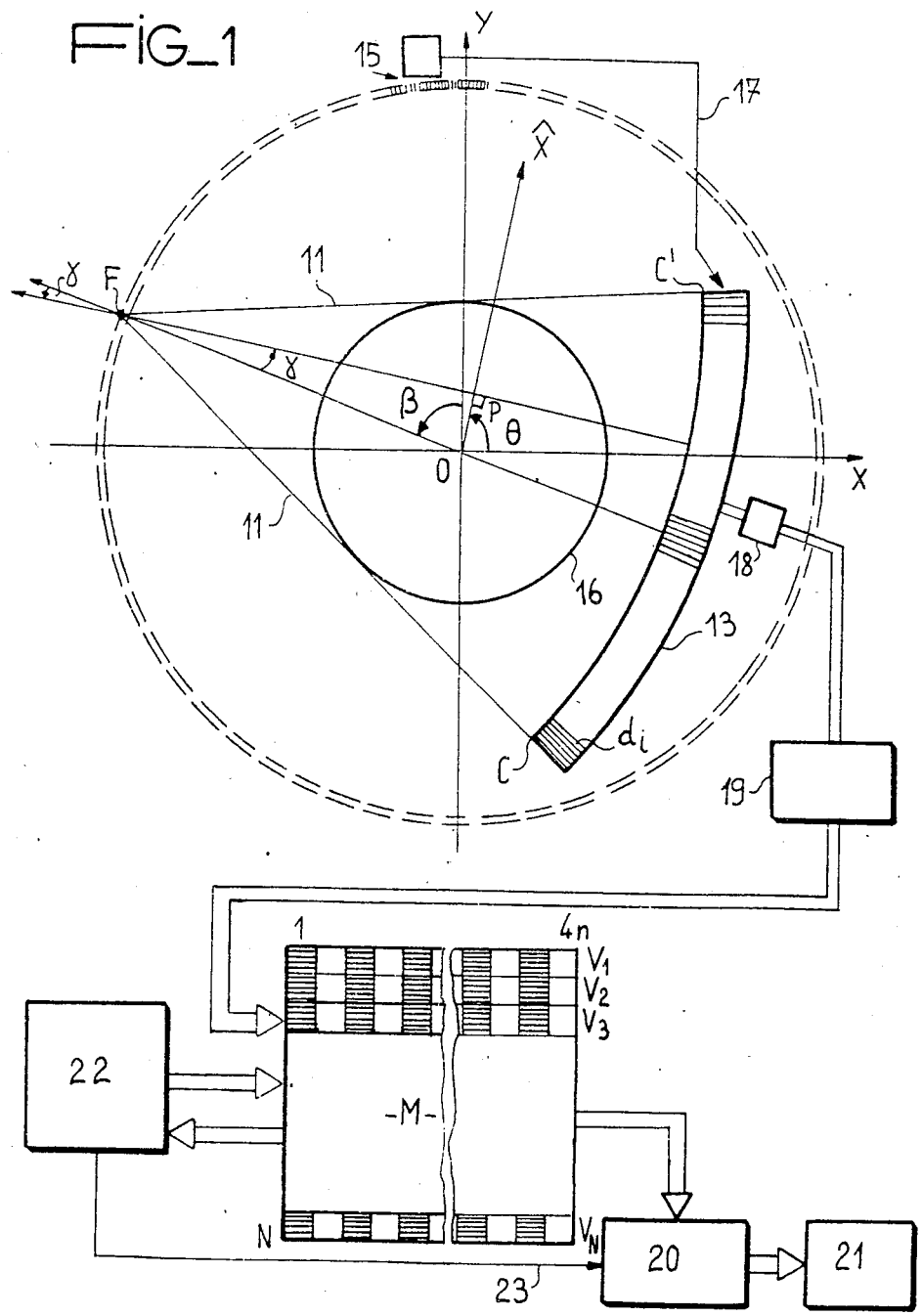

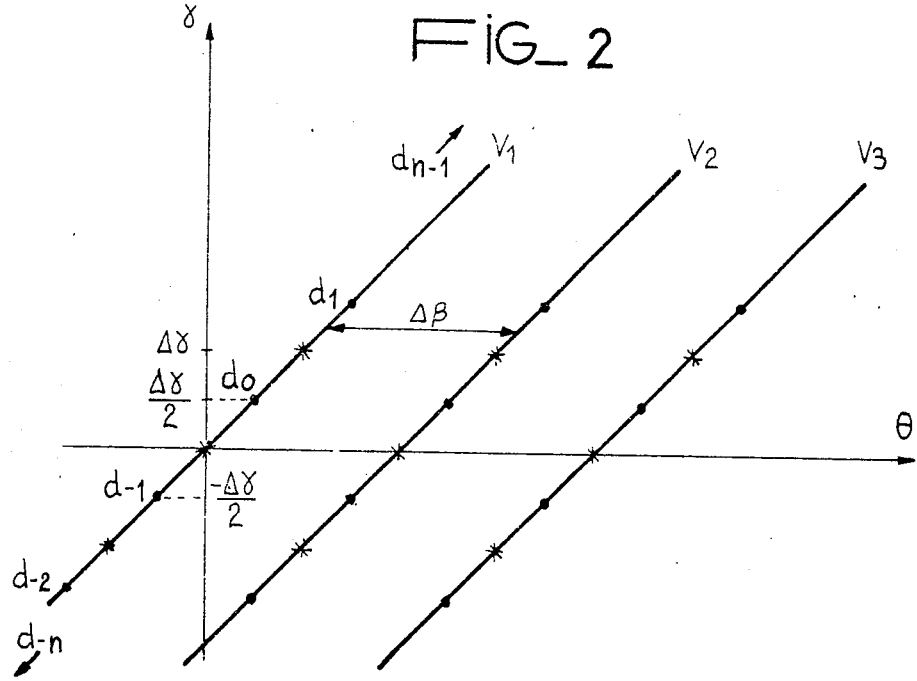
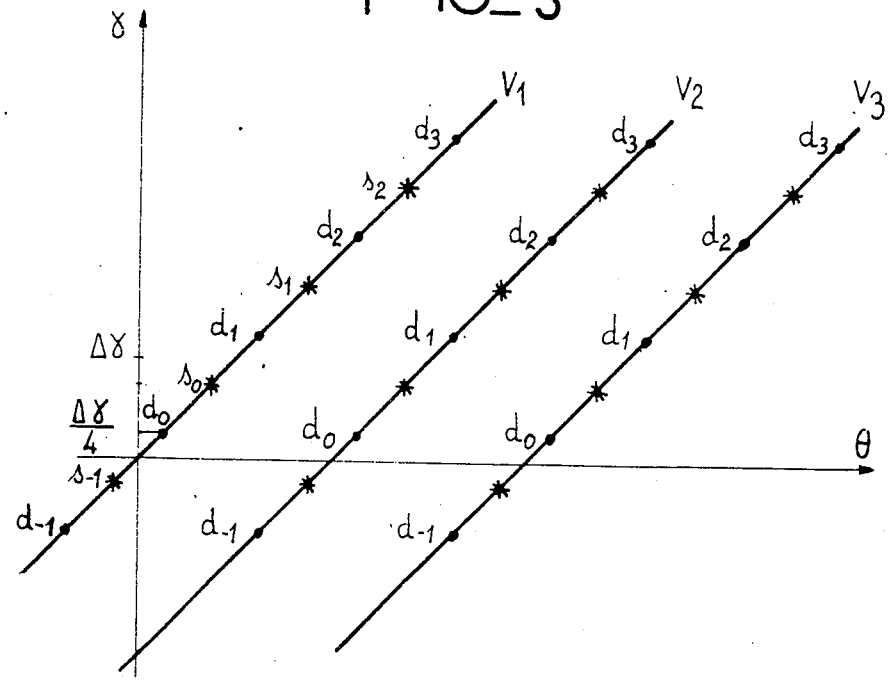

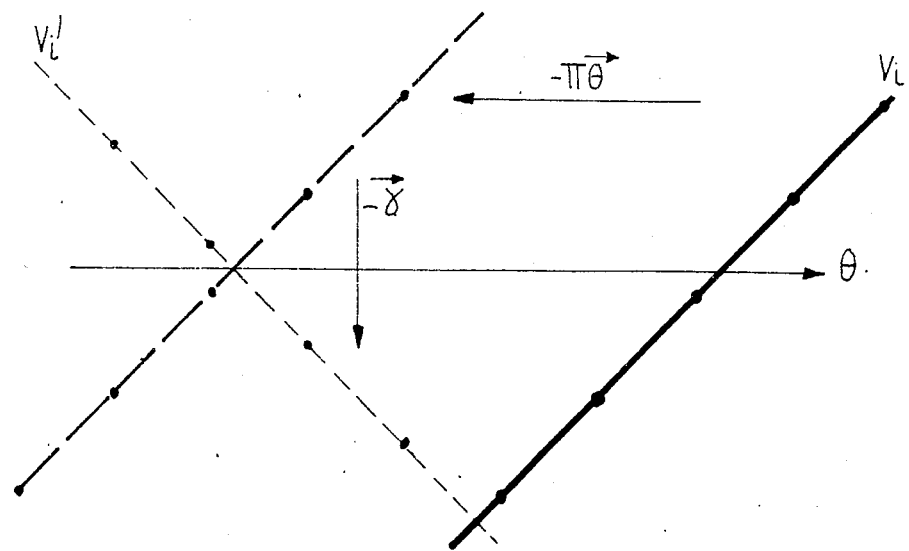
FIG_4
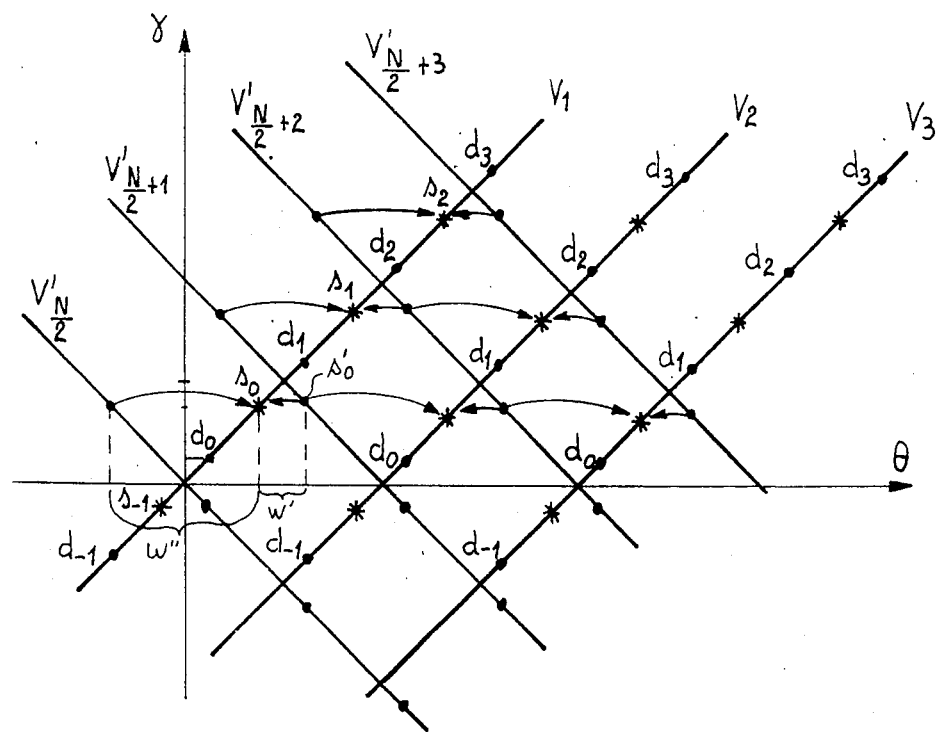
FIG_5

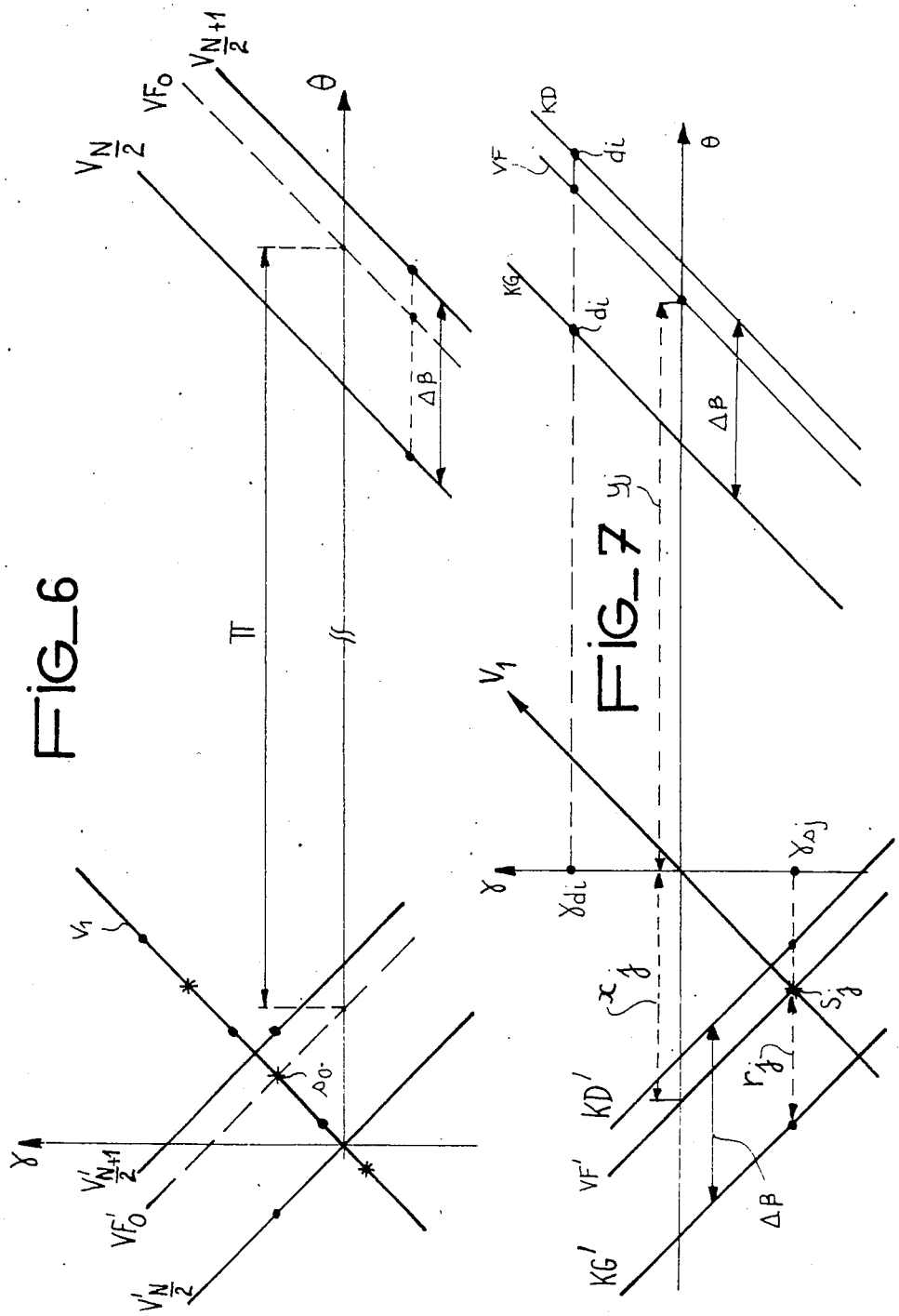

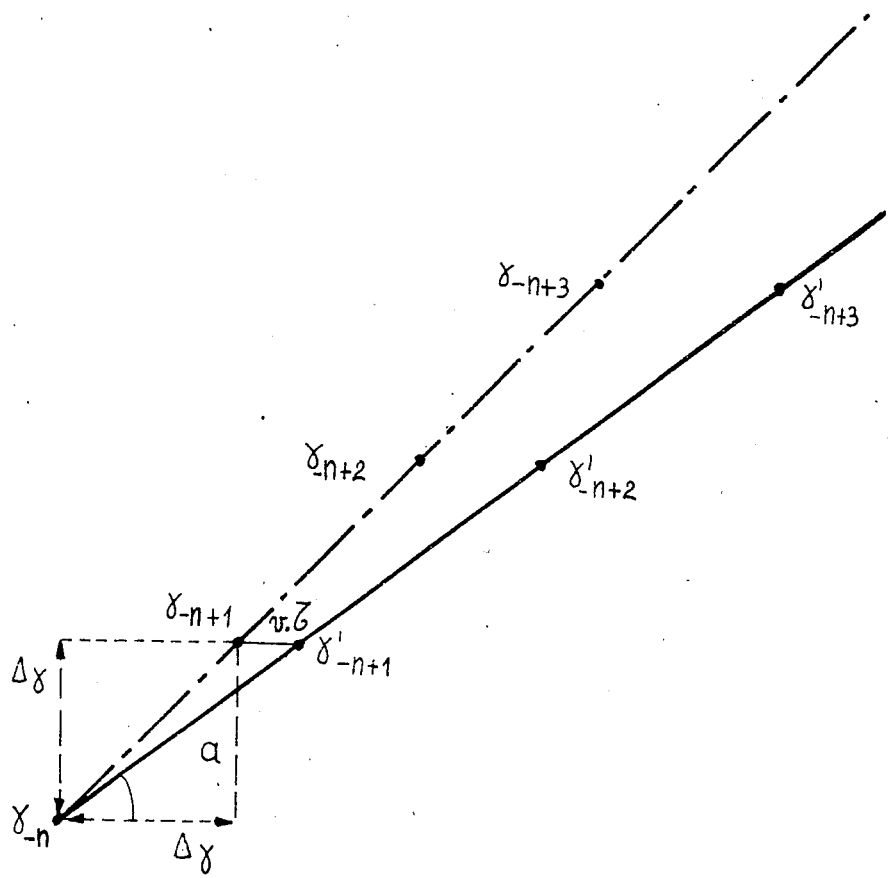
FIG_8

METHOD OF RECONSTRUCTING A HIGH RESOLUTION IMAGE BY TOMODENSITOMETRY

BACKGROUND OF THE INVENTION

1. Field of the Invention

The invention relates to a method of reconstructing a high resolution image by tomodensitometry with the purpose of improving the quality of the reconstructed image without burdening the technological structure of the means for measuring the penetrating radiation absorption and without substantially modifying the data acquisition procedure.

2. Description of the Prior Art

So called "third generation" tomodensitometers are essentially formed from a source of penetrating radiation (X rays) emitting a flat fan-shaped beam, a curved row of detectors placed opposite this source so as to measure the unabsorbed fraction of the radiation in the plane of the section of which an image is to be formed, means for rotating the source and the detectors in the plane of this section and a processor for processing the data supplied by the detectors and for reconstructing an image from this data. The spatial resolution of the reconstructed image depends more particularly on the number of detectors covering the fan shape of the X ray beam. For a given beam aperture, the higher the number of detectors the better the spatial resolution. However, the multi-detector assembly is one of the most expensive parts of the tomodensitometer and one of those which is the most difficult to produce with good reliability. Consequently, the increase in the number of detectors on a given sector corresponding to the fan shape, comes up against technological limits.

One of the aims of the invention is to substantially improve the quality of the image without modifying the technological structure of the source-detectors assembly and without substantially modifying the data acquisition procedure properly speaking.

Another aim of the invention is also to reduce the cost of construction of a tomodensitometer having spatial resolution comparable to that of existing tomodensitometers, this reduction in cost being obtained by using a multidetector assembly comprising only half the number of detectors of exising machines.

SUMMARY OF THE INVENTION

For this, the invention provides essentially a method for reconstructing images by tomodensitometry, of the type consisting in rotating a source-detectors assembly in the plane of a section the image of which it is desired to form, said source emitting a penetration radiation beam in the form of a fan and taking and storing in a memory a succession of views for different rotational angles $\beta$ of the source-detectors assembly with respect to a fixed reference axis system of said plane, the detectors being adapted so as to converge towards the focus of said source and each view being sampled for angles $\gamma$ representative of the detectors and referenced from the straight line joining the center of rotation of the source-detectors assembly and said focus, the angular shift between two adjacent detectors $\Delta\gamma$ being constant, and the angular shift between views $\Delta\beta$ being constant, which method consists, with the angular shift between said straight line and the nearest detector thereto being adjusted to $$\left|\frac{\Delta\gamma}{4}\right|,$$

in taking and storing a series of views spaced apart over a complete revolution of said source-detector assembly;

in working out for each view intermediate values representing an interlaced sampling with that of said detectors, each intermediate value, of a given angle $\gamma$, being obtained by a combination of at least two linear absorption values inferred from measurement values taken from views situated on each side of a fictitious view whose image by transformation $$T(\theta, \gamma) = (\eta + (2k-1)\pi, -\gamma)$$

contains the point representative of said intermediate value in space $[\theta,\gamma]$ with $\theta = \beta + \gamma$ and k a relative integer, said values of measurement of said views being taken from the angle detector opposite the one of said desired intermediate value; and in applying a reconstruction algorithm, known per se, comprising a convolution and back projection to the views thus completed by said intermediate values.

BRIEF DESCRIPTION OF THE DRAWINGS

The invention will be better understood from the following description of a method based on its principle and of the essential component parts of a tomodensitometer operating in accordance with this method, with reference to the accompanying drawings in which:

FIG. 1 is a schematical representation of the main component parts of a tomodensitometer for implementing the invention;

FIG. 2 is a representation in space $[\theta,\gamma]$ of the views taken by a conventional tomodensitometer operating in the pulsed mode for reconstructing an image;

FIG. 3 is a representation in the same space $[\theta,\gamma]$ of the views taken by a tomodensitometer of the same type in which one of the modifications for implementing the invention has been made, namely a static shift between the source and the detectors;

FIG. 4 illustrates, in the space $[\theta,\gamma]$

FIG. 4 illustrates, in the space $[\theta,\gamma]$ a transformation which may be applied to the views of FIG. 3 for implementing the method of the invention;

FIG. 5 illustrates in the space $[\theta,\gamma]$ the result of this transformation and shows the interpolation procedure for completing the views;

FIG. 6 illustrates the use of an algorithm in accordance with the invention, for calculating an intermediate value of the first view $V_1$;

FIG. 7 illustrates a phase in the calculation of the same algorithm; and

FIG. 8 is a representation in the space $[\theta,\gamma]$ of a view in the case of a tomodensitometer operating in continuous mode.

DESCRIPTION OF THE PREFERRED EMBODIMENT

In the rest of the description with reference to FIGS. 1 to 7 the particular case is taken of a tomodensitometer operating in pulse mode. This kind of tomodensitometer is well known. In most cases, the pulsed mode is given concrete form by the fact that the fan shaped beam is only emitted for a very brief period of time at the moment when the source-detectors assembly is at a predetermined angle $\beta$. In this case, it is sufficient for the reading of all the detectors to be finished when the source-detectors assembly reaches the next angle $\beta$. However, another way of providing said pulsed mode may consist in permanently generating the fan shaped beam but in "reading" all the detectors simultaneously at each angle $\beta$.

Referring to FIG. 1, the essential component parts of a tomodensitometer have been shown. This apparatus comprises a source-detectors assembly rotatable in a sectional plane, the image of which it is desired to form. The center of rotation is 0 and the plane of the section will be considered as being that of FIG. 1. With this sectional plane is associated a fixed reference orthonormed axis system XOY. The source is shown symbolically in the drawing by its focal plane F. It is, as is well known, a source of penetrating radiation and more particularly an x ray source emitting a fan shaped beam 11. In the rest of the text, mention will be simply made of source F. The case 13 containing all the detectors $d_i$ has a curved shaped so that these detectors are arranged along an arc of a circle $\widehat{CC'}$ centered geometrically on the focal point F. The case may of course be rectilinear but will then contain detectors arranged so as to converge towards the focal point. In the example described, the fan shaped beam 11 covers an arc of a circle $\widehat{CC'}$ occupied by the input faces of the detectors $d_i$. Thus, the reconstituted image will be inside circle 16 with center 0, inscribed within the limits of angle $\widehat{CFC'}$. An assembly may be used comprising 1024 detectors $d_i$. Case 13 and source F are fixed to the same rotary support (center of rotation 0) and are stationary with respect to each other so that rotation of the source-detectors assembly may be referenced by the angle $\beta$ between axis OY and a straight line OF. The attenuation values of the x ray beam for predetermined angles $\beta$ are inferred from the values of measurements taken at the outputs of the detectors and stored in a memory M of a processor. For each predetermined angle $\beta$ an order for reading the detectors $d_i$ is emitted, for example by means of an incremental coder 16 adapted for reading angle information related to the rotating source-detectors assembly and for delivering (drive connection 17) orders for controlling the reading of the status of all the detectors. The whole of the linear attenuation values inferred from reading the detectors for a given angle $\beta$ is called "view".

Thus, it may be considered that each view is sampled by the very structure of the detector assembly, for angles $\gamma$ representative of the detectors. Each angle $\gamma$ indicating the position of a detector $d_i$ is referenced from the straight line OF. Thus, the constant angular shift between the centers of the input faces of two adjacent detectors will be called $\Delta\gamma$.

If, for each angle $\beta$ of a view, we consider the axis $O\hat{X}$ perpendicular at P to the ray of angle $\gamma$ striking any detector, it can easily be shown that the angle $\theta$ between the axis OX of the fixed reference and the axis $O\hat{X}$ is such that:

$$\theta = \beta + \gamma$$

and this for all cases, since the angles $\theta$, $\beta$ and $\gamma$ are orientated. We have again:

$$\gamma = \theta - \beta$$

From this latter relationship, it can be seen that the different views (for different angles $\beta$) have an extremely simple representation in space $[\theta,\gamma]$.

As shown in FIG. 2, these views are carried by straight lines parallel to the first bisectrix and shifted by $\Delta\beta$ along the axis of the $\vec{\theta}$. Points may be plotted on these straight lines representing the coordinates in the space $[\theta,\gamma]$ of the sampled values effectively acquired on reading the different views.

Thus, assuming that the number of detectors is even, i.e. 2n and that the straight line OF passes exactly between the two center detectors $d_{-1}$ and $d_0$, they appear shifted by $$\left| \frac{\Delta\gamma}{2} \right|$$

on each side of the axis $\vec{\gamma}$. The aim of the invention is to obtain for each view intermediate sampled values whose coordinates in the space $[\theta,\gamma]$ are represented by stars * in FIG. 2. In other words the aim of the invention is to obtain views comprising 4n sampled values with an assembly of 2n detectors only and thus to improve the spatial resolution of the reconstructed image.

According to a feature of the invention, a permanent and predetermined angular shift between the assembly of detectors (i.e. case 13) and straight line OF is caused above all. In the example chosen, the angular shift between the straight line OF and the nearest detector ($d_0$) is chosen equal to $+(\Delta\gamma/4)$. That means that the assembly of detectors is shifted "to the left" considering FIG. 1, so that the center of the input face of detector $d_0$ is shifted angularly by $+(\Delta\gamma/4)$ with respect to OF and so that the detector $d_{-1}$ is shifted by $-(3\Delta\gamma/4)$ with respect to the same straight line.

FIG. 3 shows the configuration of the views in the space $[\theta,\gamma]$ after this shift.

For implementing the invention, a series $V_i$ is taken of N views spaced apart over a complete revolution of the source-detectors assembly, with $N=(2\pi/\Delta\beta)$.

The desired intermediate values $s_i$ are also located on the different views in FIG. 3, each intermediate value position in the space $[\theta,\gamma]$ being equidistant from the positions of two adjacent real detectors.

That is to say the transformation:

$$T(\theta,\gamma) = (\theta - \pi, -\gamma)$$

It can be shown that the function of absorption of a view is invariant for this transformation T. Now, this transformation T may be broken down in the space $[\theta,\gamma]$ in to translation $-\pi\vec{\theta}$ followed by a symmetry with respect to $\vec{\theta}$. This transformation is illustrated as such in FIG. 4. If said transformation is applied to the view $V_i$, the result is the "view" $V'_i$.

If the transformation T is thus applied to the series off views $V_i$, it can be seen that the sampled values of the transformed "views" $V'_i$ have the same ordinate $\gamma$ as the desired intermediate values $s_i$. Thus the views $V_i$ may be completed by interpolations from linear absorption values corresponding to sampled values of the "views" $V'_i$, with $\gamma$ constant, in the space $[\theta,\gamma]$, as shown by the arrows in FIG. 5. In the example, each intermediate value of a given angle $\gamma$ is obtained by a combination of two linear absorption values inferred from the sampled values having the same ordinate $\gamma$, taken from the "views" $V'_i$ situated on each side of the desired intermediate value. The combination may simply consist of a linear interpolation between the corresponding linear absorption values of two adjacent "views" $V'_i$, as shown in FIG. 5. In other words, each intermediate value is obtained by averaging these two above mentioned linear absorption values ($s_o'$ and $s_o''$), by weighting them respectively by the inverse (1/W' and 1/W'') of the difference (in projection along the axis of the $\theta$ FIG. 5) between their respective positions ($s_o'$ and $s_o''$) and the position of the desired intermediate value ($S_o$). For some "views" $V'_i$ required for the interpolation calculations suggested by FIG. 5, transformation T uses a view $V_i$ situated outside the range [$\theta,2\pi$] of the views actually acquired. However, these latter may be theoretically extended in the space [$\theta,\gamma$] from $-\infty$ to $+\infty$ because of the periodicity, with respect to $\theta$, of the linear attenuation function beyond a complete revolution (because of the condition $N=(2\pi/\Delta\beta)$, which may be represented thus:

$$V_i = V_j \longrightarrow = j \text{ Modulo } N$$

In other words, the transformation T may be completed in the following way:

$$T(\theta,\gamma) = (\theta + (2k-1)\pi, -\gamma)$$

with k a relative integer.

There always exists a value of k such that the view $V_i$ on which the translation $\theta+(2k-1)\pi$ is applied is indeed one of the views acquired $V_i$. FIG. 5 illustrates the justification of the procedure of the invention. This method of calculating the intermediate values must now be explained for the "views" $V'_i$ only represent a rearrangement of the views $V_i$ and the calculation of each intermediate value may in fact be made from each "position" of the desired intermediate value in the space [$\theta,\gamma$]. This is what is shown in FIG. 6 where only the first view $V_1$ and two "views" $V'_i$ have been shown, a result of the transformation T applied to the views $V(N/2)$ and $V(N/2)+1$ (N being even), which are also represented. The views $V(N/2)$ and $V(N/2)+1$ are situated on each side of a fictitious view $VF_o$ whose transform $VF'_o$, by the transformation T, passes through the coordinates of the intermediate value $s_o$ of the view $V_1$ in the space [$\theta,\gamma$]. According to the invention, it is therefore sufficient, for each intermediate value ($S_o$) of each view ($V_1$), to search for the corresponding "fictitious view" ($V_{Fo}$) whose transform by the transformation T passes through the coordinates of said intermediate value, to select the two adjacent real views $V_i$, $V_{i+1}$ ($V_{N/2}$, $V_{N/2+1}$) situated on each side of said fictitious view and to take from these two views the absorption values of angle $-\gamma$ ($\gamma$ being the ordinate of $s_o$ in the space [$\theta,\gamma$]) which correspond to measurement values from the same real detector and to effect a linear interpolation between these linear absorption values. It should be noted that, for the sake of simplicity, it was assumed above that the number N of acquired views $V_i$ was even; the procedure of the invention can nevertheless be applied such as it is if N is uneven.

One of the possible calculation algorithms will now be described, forming a presently preferred embodiment of the above described method. In the example described, we have the case of a "leftward" shift of the detectors, such as illustrated in the drawings and the case of a pulsed operating mode where, as is known, the sampled values of the views $V_i$ are carried by straight lines parallel to the first bisectrix of the space [$\theta,\gamma$].

With reference to FIG. 7 the algorithm will be first of all described for completing the view $V_1$. The equation of view $V_1$ is:

$$\theta = \gamma$$

It is desired to calculate the intermediate value as $s_j$.

Let $x_j$ be the difference between the intersection of the view to be completed with axis $\vec{\theta}$ (in this case the origin, in the case of view $V_1$) and the interconnection of the transform of the fictitious view (passing through $s_j$) with the same axis $\vec{\theta}$.

We have:

$$x_j = 2\gamma s_j \quad \text{(A)}$$

The point of intersection of the corresponding fictitious view with the axis of the $\vec{\theta}$ is therefore:

$$y_j = \pi + x_j \quad \text{(B)}$$

The number of the real view KG situated "on the left" of this fictitious view is therefore determined by the whole value of the ratio ($y_j/\Delta\beta$).

More precisely:

$$KG_{(j)} = E\left(\frac{y_j}{\Delta\beta}\right) + 1, \text{ modulo } N \quad \text{(C)}$$

and the number of the view KD situated "on the right" of the fictitious view is therefore:

$$KD_{(j)} = KG_{(j)} + 1, \text{ modulo } N \quad \text{(D)}$$

It now remains to determine "the ordinate $\gamma_{di}$ of a detector $\gamma_i$ to be taken into account in each view KG and KD, i.e. according to the transformation T:

$$-\gamma d_i = \gamma s_j.$$

Now, if we refer to FIG. 3:

$$\gamma d_i = (\Delta\gamma/4) + i\Delta\gamma$$

and $$\gamma s_j = -\Delta\gamma/4 + (J+1)\Delta\gamma$$

i.e.

$$= -J - 1 \quad \text{(E)}$$

Further, let $r_j$ be the rest of the operation $$E\left(\frac{y_j}{\Delta\beta}\right).$$

$r_j$ represents the difference in projection along the axis of the $\vec{\theta}$ between the position of $s_j$ and that of detector $d_j$ in the real view KG; $r_j$ is shown in FIG. 7 between the transform of the fictitious view passing through $s_j$ and the transformed KG' of KG. Consequently, from $r_j$ can be inferred the weighting to give to the linear attenuation values corresponding to the measurement values taken from the detector $d_i$ of the views KG and KD.

Let $h_{KD}(d_i)$ and $h_{KG}(d_i)$ be the linear attenuation values corresponding to detector $d_i$ in the real views $KD_{(j)}$ and $KG_{(j)}$, and let:

$$R_{(j)} = (r_j/\Delta\beta);\qquad(5)$$

It can be seen that the linear attenuation value $h(s_j)$ to be attributed to the position $s_j$ of view $V_1$ (in other words the intermediate value $s_j$ itself) is expressed:

$$h(s_j) = R_{(j)}[h_{KD}(d_i) - h_{KG}(d_i)] + h_{KG}(\hat{d_j}) \qquad (F)$$

Programming the above expressed A to F is within the scope of a man skilled in the art, as is also the design of a specialized calculating processor coupled to the buffer memory M.

To complete the following views $V_m$ (i.e. $V_2, V_3, \ldots, V_N$) we have, instead of the relationship (A):

$$x_j - (m-1)\Delta\beta = 2\gamma s_j \qquad (20)$$

that is to say:

$$x_j = 2\gamma s_j + (m-1)\Delta\beta \qquad (A')$$

The expression A' replaces A in the rearrangement and interpolation algorithm but the other relationships B to F remain unchanged. It is also interesting to note that from one view to another $R_{(j)}$ remains unchanged and that $KG_{(j)}$ is incremented by 1. Consequently, it is possible in the computing software to precompute $r$ and KG solely for the first view and then to proceed by incrementing KG. Furthermore, it can be seen that the same algorithm is valid for a "rightward" shift of the detectors, so that the method described can be applied for a shift of the detector assembly of:

$$\left|\frac{\Delta\gamma}{4}\right|.$$

The preceding algorithm was developed on the assumption of pulse mode operation. It is easy to adapt it to continuous mode operation. According to a usual continuous operating mode, it is assumed that source S emits permanently and that reading of the measurement values at the outputs of the detectors, for each view, is effected by progressive scannng from one end to the other of the assembly of detectors, for example from detector $d_{-n}$ to detector $d_{n-1}$.

Two additional parameters must be taken into consideration:

the speed of rotation $v$ of the source-detectors assembly;

the time interval $\tau$ separating the acquisition of the sampled values corresponding to two adjacent detectors, assuming a constant scanning speed.

FIG. 8 illustrates the way in which the representation of a view in the space $[\theta,\gamma]$ evolves if the parameters $v$ and $\tau$ are taken into account. The view carried by the broken straight line corresponds to the pulsed mode whereas the same view carried by the continuous straight line corresponds to the continuous mode.

The sampled values move parallel to the axis $\vec{\theta}$ since $\theta = \beta + \gamma$; $\beta$ varying during the acquisition. The two straight lines converge at $d_{-n}$ since scanning of the detectors begins by this detector and the next sampled value $d_{-n+1}$, is shifted at $d'_{-n+1}$ by a distance $v.\tau$ in the space $[\theta,\gamma]$, parallel to the axis of the $\vec{\theta}$. Let $a$ be the angle between $\overrightarrow{d_{-n}d_{-n+1}}$ and $\overrightarrow{d_{-n}d'_{-n+1}}$.

$$\tan a = \frac{\Delta\gamma}{\Delta\gamma + v\cdot\tau} = \frac{1}{1+\frac{v\cdot\tau}{\Delta\gamma}}$$

i.e.

$$\alpha = \frac{v\cdot\tau}{\Delta\gamma}, \tan a = \frac{1}{1+\alpha}$$

The views are therefore carried by straight lines parallel to the straight line of equation $\theta = (1+\alpha)\gamma$ Consequently, for the view $V_1$, the relationship (A) becomes:

$$x_j = 2(1+\alpha)\gamma s_j$$

and for any view $V_m$, the relationship (A') becomes:

$$x_j = 2(1+\alpha)\gamma s_j + (m-1)\Delta\beta.$$

The rest of the algorithm is applied without modification with the new above defined values of $x_j$.

It can be seen that the method described can also be applied without change whatever the type of continuous mode scanning. In this case, the sample values of the views are no longer necessarily carried by straight lines but by any curves to which the same transformation T may be applied so as to infer therefrom the desired intermediate values from interpolations similar to those described above.

Referring again to FIG. 1, the essential parts of the computer associated with detectors $d_i$ are shown in the form of a functional block diagram. The sampled values read at the outputs of the detectors $d_i$ are transformed into digital information by means of an analog-digital converter 18 then processed in a preprocessor 19 carrying out the usual calibration and logarithmic transformation operations. The information thus transformed is formed by the corresponding linear attenuation values and this digital information is stored in memory M.

For reasons which will be more clearly understood further on, memory M is in the form of a matrix of storage units comprising 4n columns and N lines (number of views $V_i$) since the acquisition of the views $V_i$ is made during a complete revolution and with: $\Delta\beta = (2\pi/N)$.

Filling of memory M with the information representative of the views $V_i$ occurs on the basis of one storage unit out of two; these units are shown by hatching in FIG. 1. Filling of memory M, such as shown, corresponds to a "leftward" shift of the detectors. Memory M is associated with reading means 20 which organize the transfer of information to a processor 21, known per se, and whose role is to apply the above mentioned reconstruction algorithm. However, reading of a line of memory M is only ordered when all the storage units of this line which have not been "filled" during the phase for storing the views $V_i$, have received digital information representative of the intermediate values, calculated using the above described algorithm. For that, a specialized processor or a sub program of the computer effects the computing, addressing in memory M and linear interpolation operations before ordering writing of the resulting intermediate values in the storage units left temporarily "empty" during writing of the real views in the same memory M.

This processor or this sub program is shown symbolically in FIG. 1 by the functional block 22 adapted for calculating the addresses of the useful linear attenuation values, reading these values, effecting the interpolation calculation combining these values and rewriting the result at the suitable address of an intermediate value of a view to be completed. It also drives the reading means 20 (functional connection 23) controlling the transfer of information from memory M to the reconstruction processor 21, the transfer of a "line" from the memory only being permitted when all the storage units corresponding to the intermediate values have been filled.

What is claimed is:

1. A method of reconstructing images by tomodensitometry, of the type having a source-detectors assembly, the method comprising rotating a source-detectors assembly in the plane of a section whose image it is desired to form, said source emitting a penetrating radiation beam in the form of a fan and taking and storing a succession of views for different rotational angles $\beta$ of the source-detectors assembly with respect to a fixed reference axis system (XOY) of said plane, a plurality of detectors being arranged so as to converge towards the focal point (F) of said source and each view being sampled for angles $\gamma$ representative of the detectors and referenced from a straight line (OF) joining a center of rotation (0) of the source-detectors assembly and said focal point (F), an angular shift between two adjacent detectors $\Delta\gamma$ being constant and an angular shift between views being constant, with the angular shift between said straight line (OF) and the nearest detector thereto adjusted to $$\left|\frac{\Delta\gamma}{4}\right|$$

and taking and storing a series of views spaced apart over a complete revolution of said source-detectors assembly, measuring for each view a number of intermediate values representing sampling interlaced with that of said detectors, each intermediate value of a given angle $\gamma$ being obtained by a combination of at least two linear absorption values inferred from measured values taken from the views situated on each side of a fictitious view whose image by a transformation T $(\theta,\gamma)=(\theta+(2k-1)\pi,-\gamma)$ contains a point representative of said intermediate value in a space $[\theta,\gamma]$ with $\theta=\beta+\gamma$ and k a relative integer, said measured values of said views being taken from an angle detector opposite one of said desired intermediate value, and applying a reconstruction algorithm, comprising a convolution and a rear projection to the views thus completed by said intermediate values.

2. The reconstruction method as claimed in claim 1, wherein said combination consists for each intermediate value, in averaging the two linear absorption values by weighting them respectively by the inverse of the distance along axis $\vec{\theta}$ in the space $[\theta,\gamma]$, between their respective positions resulting from said transformation T and the position of the intermediate value considered.

* * * * *